US007373968B2

(12) United States Patent
Oldenburg

(10) Patent No.: US 7,373,968 B2
(45) Date of Patent: *May 20, 2008

(54) METHOD AND APPARATUS FOR MANIPULATING AN ORGANIC LIQUID SAMPLE

(75) Inventor: Kevin R. Oldenburg, 665 Riverpoint Blvd., Spokane, WA (US) 99202

(73) Assignee: Kevin R. Oldenburg, Spokane, WA (US)

( * ) Notice: Subject to any disclaimer, the term of this patent is extended or adjusted under 35 U.S.C. 154(b) by 585 days.

This patent is subject to a terminal disclaimer.

(21) Appl. No.: 10/893,565

(22) Filed: Jul. 16, 2004

(65) Prior Publication Data

US 2005/0034849 A1 Feb. 17, 2005

Related U.S. Application Data

(63) Continuation-in-part of application No. 10/356,687, filed on Jan. 31, 2003, now Pat. No. 7,025,120, and a continuation-in-part of application No. PCT/US03/00476, filed on Jan. 8, 2003, and a continuation-in-part of application No. 10/041,703, filed on Jan. 8, 2002, now abandoned.

(51) Int. Cl.
*F28F 27/00* (2006.01)
*C12M 1/36* (2006.01)

(52) U.S. Cl. ...................... 165/200; 165/269; 422/109; 422/127; 435/286.1; 435/288.3; 435/288.4; 435/305.3

(58) Field of Classification Search ................ 165/253, 165/269, 61, 200; 422/101, 102, 109, 127, 422/128; 435/286.1, 286.6, 288.3, 288.4, 435/305.1, 305.2, 305.3, 305.4, 809
See application file for complete search history.

(56) References Cited

U.S. PATENT DOCUMENTS

| | | | | |
|---|---|---|---|---|
| 1,006,787 | A | 10/1911 | Pratt | |
| 1,456,005 | A | 5/1923 | Harris | |
| 2,379,474 | A | 7/1945 | Bramson | 237/3 |
| 3,379,118 | A | 4/1968 | Perez | 99/419 |
| 3,616,264 | A | 10/1971 | Ray et al. | 195/127 |
| 4,038,055 | A | 7/1977 | Varano et al. | 55/197 |
| 4,116,777 | A | 9/1978 | Takátsy et al. | 195/127 |
| 4,286,456 | A | 9/1981 | Sisti et al. | 73/23.1 |
| 4,420,679 | A | 12/1983 | Howe | 219/400 |
| 4,468,423 | A | 8/1984 | Hall | 428/72 |

(Continued)

OTHER PUBLICATIONS

Cao, T., "A simple and inexpensive system to amplify DNA by PCR," *Biotechniques*, 7(6):566-7, Jun. 1989.

(Continued)

*Primary Examiner*—Ljiljana Ciric
(74) *Attorney, Agent, or Firm*—Seed Intellectual Property Law Group PLLC

(57) ABSTRACT

A lid for a well plate, which has pins that penetrate the lid and project downwardly into the wells of the well plate. Thermal energy is applied to the upper end of the pin to regulate the temperature of liquid samples. Ultrasonic energy is applied to the upper end of the pin to sonicate the liquid sample. An electrical charge is applied to the upper end of the pin to attract charged materials, such as DNA, and to selectably segregate charged materials from the liquid sample.

18 Claims, 12 Drawing Sheets

U.S. PATENT DOCUMENTS

| | | | | |
|---|---|---|---|---|
| 4,481,405 | A | 11/1984 | Malick | 219/405 |
| 4,683,195 | A | 7/1987 | Mullis et al. | 435/6 |
| 4,683,202 | A | 7/1987 | Mullis | 435/91 |
| 4,687,636 | A | 8/1987 | Hart | 422/57 |
| 4,701,415 | A | 10/1987 | Dutton et al. | 435/289 |
| 4,827,780 | A | 5/1989 | Sarrine et al. | 73/864.21 |
| 4,865,986 | A | 9/1989 | Coy et al. | 435/290 |
| 4,889,818 | A | 12/1989 | Gelfand et al. | 435/194 |
| 4,891,321 | A | 1/1990 | Hubscher | 435/293 |
| 4,902,624 | A | 2/1990 | Columbus et al. | 435/316 |
| 4,965,188 | A | 10/1990 | Mullis et al. | 435/6 |
| 4,981,801 | A | 1/1991 | Suzuki et al. | 435/290 |
| 5,038,852 | A | 8/1991 | Johnson et al. | 165/12 |
| 5,061,630 | A | 10/1991 | Knopf et al. | 435/290 |
| 5,200,084 | A | 4/1993 | Liberti et al. | 210/695 |
| 5,236,666 | A | 8/1993 | Hulette et al. | 422/65 |
| 5,333,675 | A | 8/1994 | Mullis et al. | 165/12 |
| 5,432,086 | A | 7/1995 | Frä nzl et al. | 435/291 |
| 5,455,175 | A | 10/1995 | Wittwer et al. | 435/286.1 |
| 5,489,532 | A | 2/1996 | Charm et al. | 435/286.1 |
| 5,525,300 | A | 6/1996 | Danssaert et al. | 422/99 |
| 5,601,141 | A | 2/1997 | Gordon et al. | 165/263 |
| 5,602,756 | A | 2/1997 | Atwood et al. | 364/500 |
| 5,604,130 | A | 2/1997 | Warner et al. | 435/286.7 |
| 5,681,492 | A | 10/1997 | Van Praet | 219/400 |
| 5,716,842 | A | 2/1998 | Baier et al. | 435/283.1 |
| 5,721,136 | A | 2/1998 | Finney et al. | 435/287.2 |
| 5,770,151 | A | 6/1998 | Roach et al. | 422/63 |
| 5,819,842 | A | 10/1998 | Potter et al. | 165/206 |
| 5,863,507 | A | 1/1999 | James | 422/104 |
| 5,939,312 | A | 8/1999 | Baier et al. | 435/287.2 |
| 6,083,763 | A | 7/2000 | Balch | 436/518 |
| 6,086,821 | A | 7/2000 | Lee | 422/20 |
| 6,101,946 | A | 8/2000 | Martinsky | 101/494 |
| 6,153,426 | A | 11/2000 | Heimberg | 435/287.2 |
| 6,171,850 | B1 | 1/2001 | Nagle et al. | 435/286.1 |
| 6,197,575 | B1 | 3/2001 | Griffith et al. | 435/288.4 |
| 6,207,369 | B1 | 3/2001 | Wohlstadter et al. | 435/6 |
| 6,277,332 | B1 | 8/2001 | Sucholeiki | 422/128 |
| 6,312,960 | B1 | 11/2001 | Balch et al. | 436/518 |
| 6,331,441 | B1 | 12/2001 | Balch et al. | 436/518 |
| 6,338,802 | B1 | 1/2002 | Bodner et al. | 210/650 |
| 6,372,486 | B1 | 4/2002 | Fripp | 435/303.1 |
| 6,423,536 | B1 | 7/2002 | Jovanovich et al. | 435/287.2 |
| 6,451,261 | B1 | 9/2002 | Bodner et al. | 422/99 |
| 6,479,301 | B1 | 11/2002 | Balch et al. | 436/518 |
| 6,489,112 | B1 | 12/2002 | Hadd et al. | 435/6 |
| 6,627,421 | B1 | 9/2003 | Unger et al. | 435/173.5 |
| 6,640,891 | B1 * | 11/2003 | Oldenburg | 165/253 |
| 6,948,843 | B2 | 9/2005 | Laugharn, Jr. et al. | 366/127 |
| 7,025,120 | B2 * | 4/2006 | Oldenburg | 165/11.1 |

OTHER PUBLICATIONS

Chapin, K., et al., "Evaluation of a rapid air thermal cycler for detection of Mycobacterium tuberculosis," *J. Clin Microbiol.*, 35(8):2157-9, Aug. 1997.

Civitello, A., et al., "A simple protocol for the automation of DNA cycle sequencing reactions and polymerase chain reactions," *DNA Seq.*, 3(1):17-23, 1992.

Constants, A., "Some like it hot: A thermal cycler roundup," The Scientist, 15(24):32, Dec. 10, 2001, pp. 1-7.

Denton, et al., *PCR Protocols: A Guide to Methods and Applications*, "A Low-Cost Air Driven Cycling Oven," pp. 435-441.

Mai,M., et al., "Shortened PCR cycles in a conventional thermal cycler," *Biotechniques*, 25(2):208-10, Aug. 1998.

Merriam-Webster's Collegiate Dictionary, Tenth Edition, Merrimam-Webster, Incorporated, 1996, p. 959.

Perry and Green, *Perry's Chemical Engineer's Handbook 7th Ed.*, "Heat Transfer by Radiation," pp. 5-23 to 5-42.

Soper,S., et al., "Sanger DNA-sequencing reactions performed in a solid-pahse nanoreactor directly coupled to capillary gel electrophoresis," *Anal Chem., 70*(19):4036-43, Oct. 1, 1998.

Tret'iaov, A., et al., "Fast DNA amplification in smalll ultrthin-wall microplates," *Bioorg Khim., 23*(6):526-8, Jun. 1997.

Weis, J., et al., "Detection of rare mRNAs via quantitative RT-PCR," *Trends Genet.*, 8(8):263-4, Aug. 1992.

Wilding, p., et al., "PCR in a silicon microstructure," *Clin Chem.*, 40(9):1815-8, Sep. 1994.

Wittwer, C., et al., "Minimizing the time required for DNA amplification by efficient heat transfer to small samples," *Anal Biochem*, 86(2):328-31, May 1, 1990.

Wittwer, C., et al., "Rapid cycle DNA amplification: time and temperature optimization," *Biotechniques*, 10(1):76-83, Jan. 1991.

* cited by examiner

METHOD AND APPARATUS FOR MANIPULATING AN ORGANIC LIQUID SAMPLE

CROSS-REFERENCE TO RELATED APPLICATIONS

This application claims the benefit of U.S. patent application Ser. No. 10/356,687 filed Jan. 31, 2003, which is a Continuation-In-Part of PCT Application No. PCT/US03/00476 filed Jan. 8, 2003 which is a Continuation-In-Part of U.S. patent application Ser. No. 10/041,703 filed Jan. 8, 2002 Rapid Thermal Cycling Device.

FIELD OF THE INVENTION

The invention relates to an apparatus and method for purifying ions in a liquid sample. The invention of the present application also addresses an apparatus and method for applying ultrasound energy to a liquid sample.

DESCRIPTION OF THE RELATED ART

It is desirable to have the capability to apply ultrasonic energy to liquid samples contained in the wells of a well plate. Well plates containing wells for 96, 384 and 1536 liquid samples currently are available. As used herein, the term "liquid" refers to pure liquids, as well as liquids containing particulate matter (especially biological material containing for example, proteins, DNA, or cells) and solvents containing solute. Ultrasound (ultrasonic energy) has been used for many years as a method to shear large molecules into smaller fragments and to disrupt plant or animal cells, thereby releasing the cellular contents into solution. Ultrasound also has been used to assist in the solubilization of compounds or chemicals and to promote chemical reactions. A number of different sonicators currently are available. A 'sonicator' is an instrument that transmits ultrasound into a solution or material. Sonicator systems usually are comprised at a minimum of a controller, amplifier and sonic horn. The horn is typically shaped to maximally transmit the ultrasound energy into the desired sample. A "microtip" horn has been produced and is available commercially. The microtip horn directs ultrasound energy to a single tip that can be inserted into a liquid sample. The microtip horn can be used to sonicate small samples either in tubes or individual wells of a well plate.

The microtip horn suffers from the deficiency that it can sonicate only one sample at a time, not the, say, 1536 samples in a well plate with 1536 wells. Microtip horns also suffer from the problem that the tip tends to shear away from the main body of the horn due to the high energy input into the small-diameter tip. In addition, the horn cannot be reliably cleaned between uses to avoid cross contamination of the samples.

It is desirable to have the capability to segregate ions in liquid samples in wells in a well plate based on the electrical charge of the ions. For example, during PCR or Cycle Sequencing of DNA, reaction components are removed from the solution prior to subsequent steps and DNA that has been amplified must be purified (segregated) from the unused reactants and other products. Nucleic acid amplification is typically performed by thermal cycling reactions in the presence of a thermostable DNA polymerase such as Taq Polymerase. The solution in which the amplification occurs typically contains many different components including but not limited to, a buffer, nucleotide triphosphates, magnesium chloride, potassium chloride, dithiothreotol, DNA, oligonucleotides, and the DNA polymerase (e.g. Taq). Once the amplification process of the DNA is complete, the reaction solution contains not only the components listed above but reaction byproducts as well. The amplified nucleic acid must then be purified from this mixture before additional steps can be performed. There are a number of methods by which DNA can be purified including size exclusion chromatography, gel electrophoresis, and ion exchange chromatography. Other typical methods to "purify" the DNA all are modifications of the above three methods. All of the currently available methods to "purify" the DNA products from solution require multiple additional steps and transfer of the product solution from the original reaction container into at least one additional container. It would be beneficial to be able to perform both nucleic acid amplification and purification in the same well of a well plate serially and without further additions to the well.

In ion exchange chromatography, molecules of one charge (either positive or negative) are attracted to molecules of the opposite charge that are immobilized onto a solid support, usually a glass particle or insoluble organic support. The insoluble support material is then serial "washed" with solutions containing higher and higher concentrations of a specific salt (typically sodium chloride). As the salt concentration increases, the ions in the salt solution "compete" for the ion binding sites on the solid support with the result that at low salt concentrations, molecules with low net charge are competed from (released from) the solid support while molecules with higher net charges remain bound to the solid support.

Nucleic Acids, including Deoxyribonucleic Acid (DNA) and Ribonucleic Acid (RNA), are polymeric anions. As such, they will be attracted by insoluble supports that contain a positive charge (cathodes) and repelled by insoluble supports that contain a negative charge (anodes). Nucleic Acids have been successfully purified from heterogeneous solutions by ion exchange chromatography using various types of insoluble support materials. Typically, this is done through the addition of an ion exchange material into the solution containing the nucleic acid and manipulation of the ionic strength of the solution through the addition of small inorganic ions to allow binding of the nucleic acid to the insoluble support. Once binding of the nucleic acid to the insoluble support has occurred, the solution, and hence the "impurities", are removed from the soluble support by sequential "washing" of the support. By manipulating the ionic strength of the wash solution, some means of control over the size (length) of the nucleic acid polymer that remains attached to the support can be achieved. The ions in the wash solution compete for binding to the surface charge on the insoluble support with the nucleic acid and hence, the degree of nucleic acid binding can be crudely regulated by changing the concentration of ion in the wash solution. At a relatively low ionic strength (e.g. Distilled water) nucleic acid binding to the insoluble support is nearly independent of size. As the ionic strength of the wash solution increases, the shorter length nucleic acid polymers will elute from the support first, followed by longer polymers as the ionic strength of the wash solution increases.

One of the major problems with the current methods and devices for purification by ionic interaction is that the support materials have a fixed surface charge that cannot be changed. The support materials are usually described in terms of "weak," "moderate," or strong anion/cation exchange resins. Each of these "resins" is actually a different material with different physical properties. In order to change the surface charge, different materials are used as the support, or counter ions are used to effectively mask the charge.

SUMMARY OF THE INVENTION

U.S. patent application Ser. No. 09/655,021 entitled Rapid Thermal Cycling Device filed on Sep. 5, 2000 and U.S. patent application Ser. No. 10/041,703 entitled Rapid Thermal Cycling Device filed Jan. 8, 2002 teach generally the use of a lid for a well plate, the lid having pins depending from the lid for insertion into the wells of a well plate. The pins extend from the upper side of the lid through the lid and into the wells of the well plate, the pins contacting the liquid samples in the wells. The upper side of the pinned lid is in thermal communication with the liquid samples through the pins, allowing control of the temperature of the liquid samples by application of heat to or removal of heat from the upper side of the lid.

As used in this application, the term "pin" means any elongated member. For purposes of this application, a lid having pins consistent with the present invention is referred to as a "pinned lid."

The present Invention provides for the sonication of liquid samples contained in a well plate, for example a well plate having 1536 wells with each well having a volume of 6 μl. A pinned lid is provided for the well plate. A sonic horn applies ultrasonic energy to the ends of the pins on the upper side of the lid. Each pin transmits ultrasonic energy from the upper side of the lid to each liquid sample, sonicating each liquid sample. A resilient gasket may be applied to the lower side of the lid to segregate the contents of each well from the contents of every other well in the well plate. Pins may be resiliently mounted to the lid so as to allow movement of the pins in a direction normal to the plane of the lid, allowing the pins to move in response to pressure applied by a peltier device or sonic horn. Resiliently mounted pins allow the peltier device or sonic horn to contact all of the pins.

The present Invention provides for segregation of ions having different electrical charges in liquid samples contained in wells of a well plate. A well plate is provided with a pinned lid. Each pin is composed of, coated with, or includes on its surface a material that is capable of being electrically charged; that is, of containing a net electrical charge on its surface. An electrical charge, for example a positive charge, is applied to a pin. Since the pin is in contact with the liquid sample, any negatively charged ions will be attracted to and bound to the positively charged pins. By varying the net positive charge on the pins, molecules of differing net negative charge can be isolated. For example, initially, a high net positive charge may be imparted onto the pins causing the majority of negatively bound ions in the reaction solution to be bound to the pin. The pin can then be removed from the solution and placed into another solution (water, buffer, etc.) and the net positive charge on the pin decreased with the result that molecules with a low net negative charge will be released into solution. This process can be repeated as necessary in order to segregate the desired molecules. The segregation of a material from the liquid sample in a well of a well plate by application of an electrical charge to a pin is referred to in this application as "electrical charge segregation."

The present Invention also is an apparatus and method for selectively applying any of the steps of thermal cycling, sonication or electrical charge segregation in any sequence to a liquid sample contained in a well of a well plate.

BRIEF DESCRIPTION OF THE DRAWINGS

The accompanying drawings, which are incorporated in and form a part of the specification, illustrate the embodiments of the present invention and, together with the description, serve to explain the principles of the invention.

DESCRIPTION OF THE PREFERRED EMBODIMENT

In describing an embodiment of the invention, specific terminology will be selected for the sake of clarity. However, the invention is not intended to be limited to the specific terms so selected, and it is to be understood that each specific term includes all technical equivalents that operate in a similar manner to accomplish a similar purpose.

Figure 1:
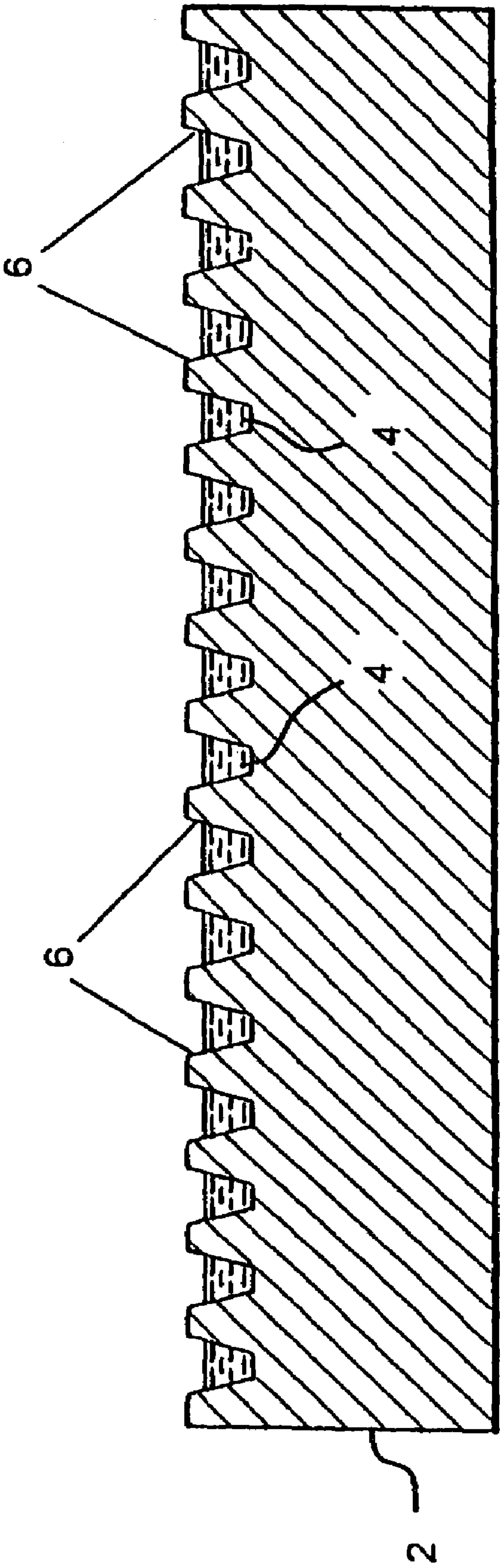
FIG. 1 is a well plate containing liquid samples
Figure 4:
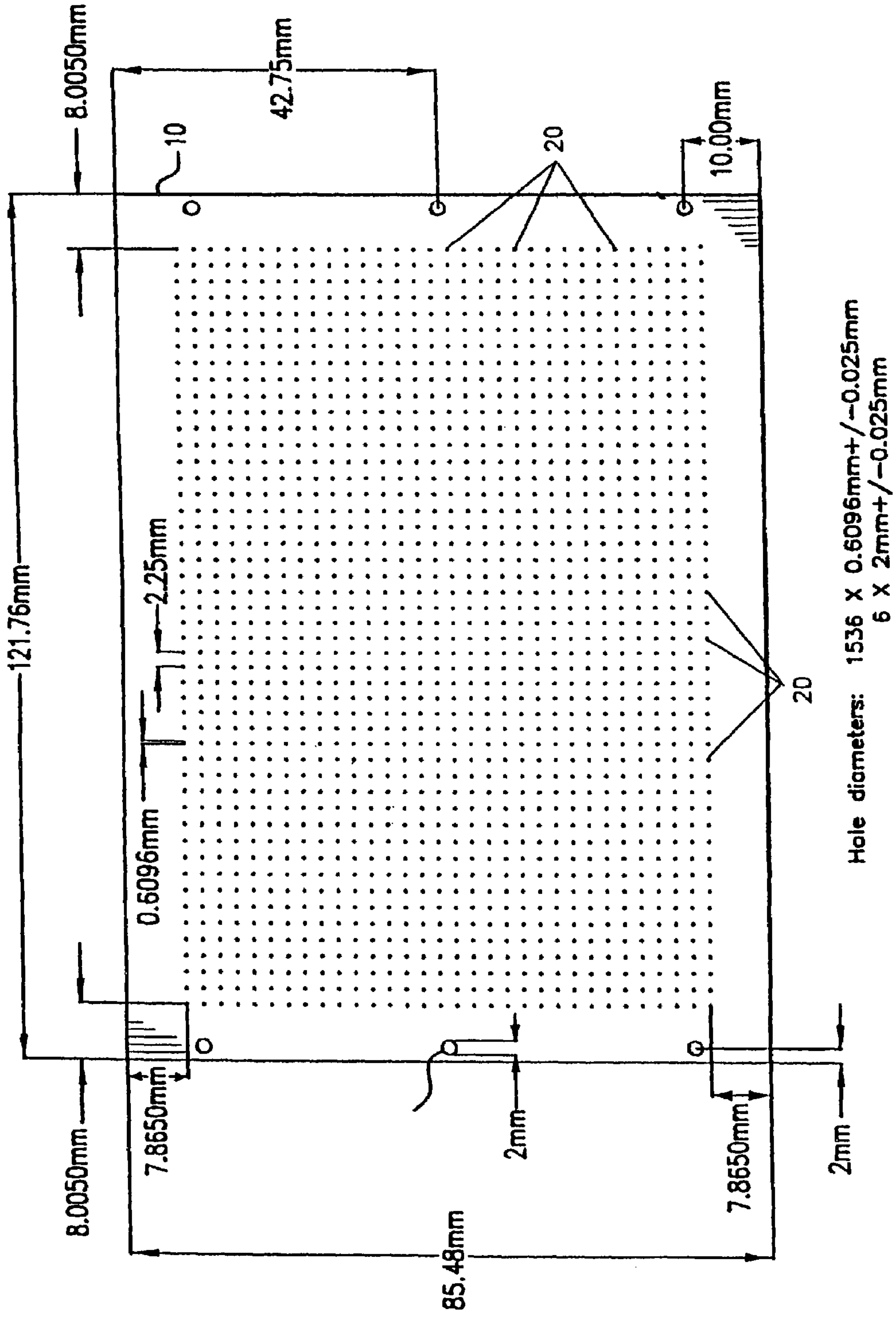
FIG. 4 is a plan view of a lid showing holes to receive pins.

From FIG. 1, a well plate 2 is a container for the simultaneous manipulation of numerous liquid samples 4 contained in wells 6. A pinned lid 10 is provided for the well plate 2. The pinned lid 10 covers each of the wells 6 in the well plate 2 and serves to prevent evaporation of the liquid samples 4 or contamination of a liquid sample 4 by another liquid sample 4. The lid 10 may be composed of a circuit board material or of any other sufficiently rigid material 12 and may be injection molded. Pins 14 (FIG. 2A) penetrate the lid 10. Each of the pins 14 has an upper end 16 and a lower end 18 (FIG. 2B). The upper end 16 of a pin 14 penetrates the lid 10 through a hole 20 (FIG. 4) in the lid 10.

Figure 2B:
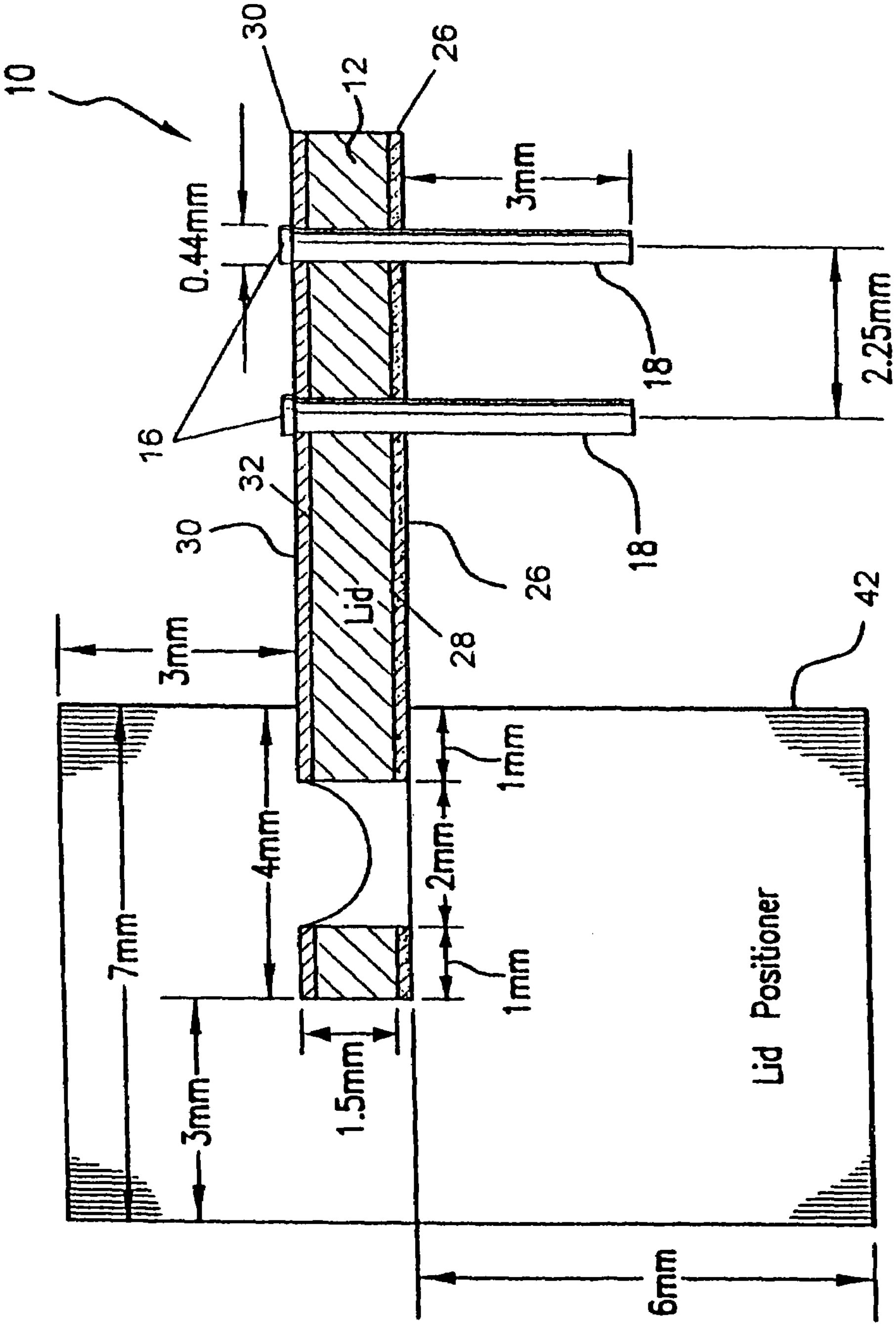
FIG. 2B is an enlarged view of a pinned lid.
Figure 3:
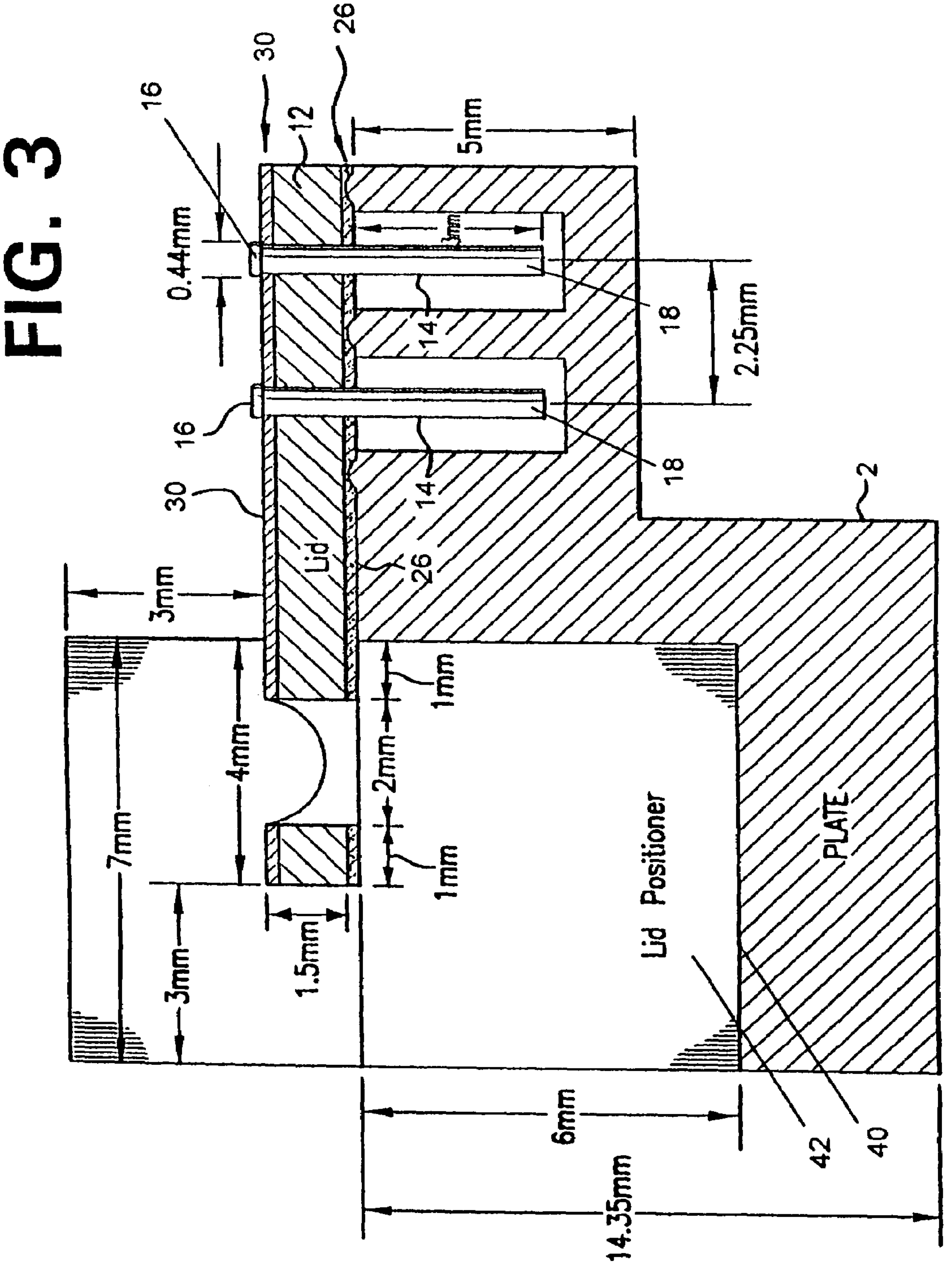
FIG. 3 illustrates a pinned lid installed on a well plate.

The lid 10 engages well-plate 2. Ears 22 (FIG. 2B) on the lid 10 mate with slots 24 (FIG. 3) on the well plate 2 to accurately locate and guide the lid 10 so that the pins 14 do not touch the well plate 2 during installation or removal of the lid 10 from the well plate 2. When the lid 10 is installed on the well plate 2, each pin 14 projects into a well 6 of the well plate 2. A pin 14 may physically contact the liquid sample 4 contained in the well 6 into which the pin 14 is inserted.

A gasket 26 (FIGS. 2B, 3) may be provided to seal the lid 10 against the wells 6 of the well plate 2, inhibiting evaporation of the liquid sample 4 during repeated heating and cooling of the sample 4 during thermal cycling. The gasket 26 is composed of a resilient material, such as silicone rubber. The gasket 26 may appear as a thin layer of resilient material applied to the lower side 28 of the lid 10. The gasket 26 also is useful in preventing microparticulate drops of liquid sample 4 from moving from one well 6 to an adjacent well 6 during sonication. The degree of sealing of the wells 6 required may vary with the application. Depending on the application, the lid 10 may be provided with a gasket 26 under the entire lid 10, a perimeter gasket 26 only, or no gasket 26 at all.

Figure 9:
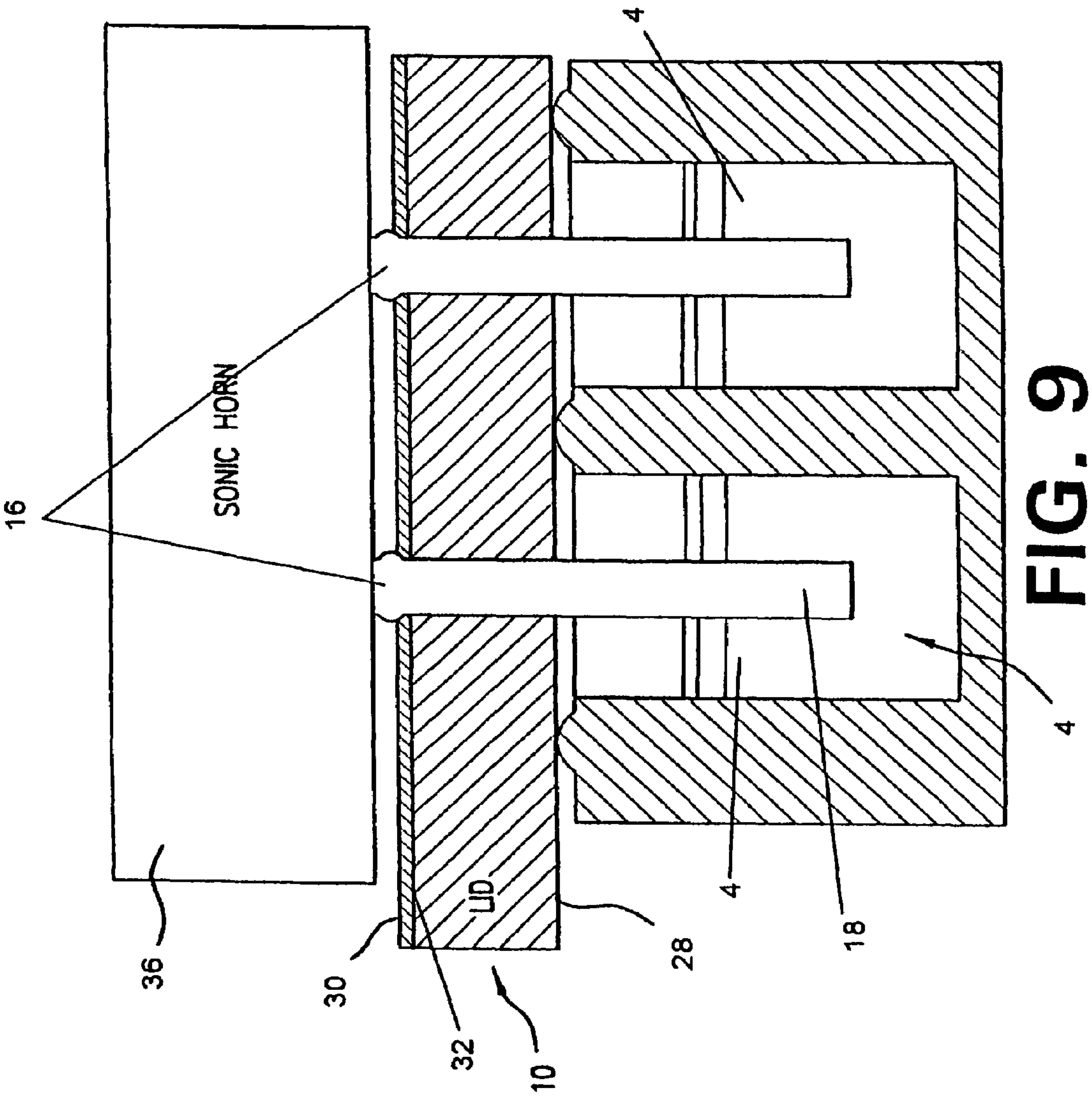
FIG. 9 is a schematic showing application of sonic energy to the pins by a sonic horn.
Figure 10:
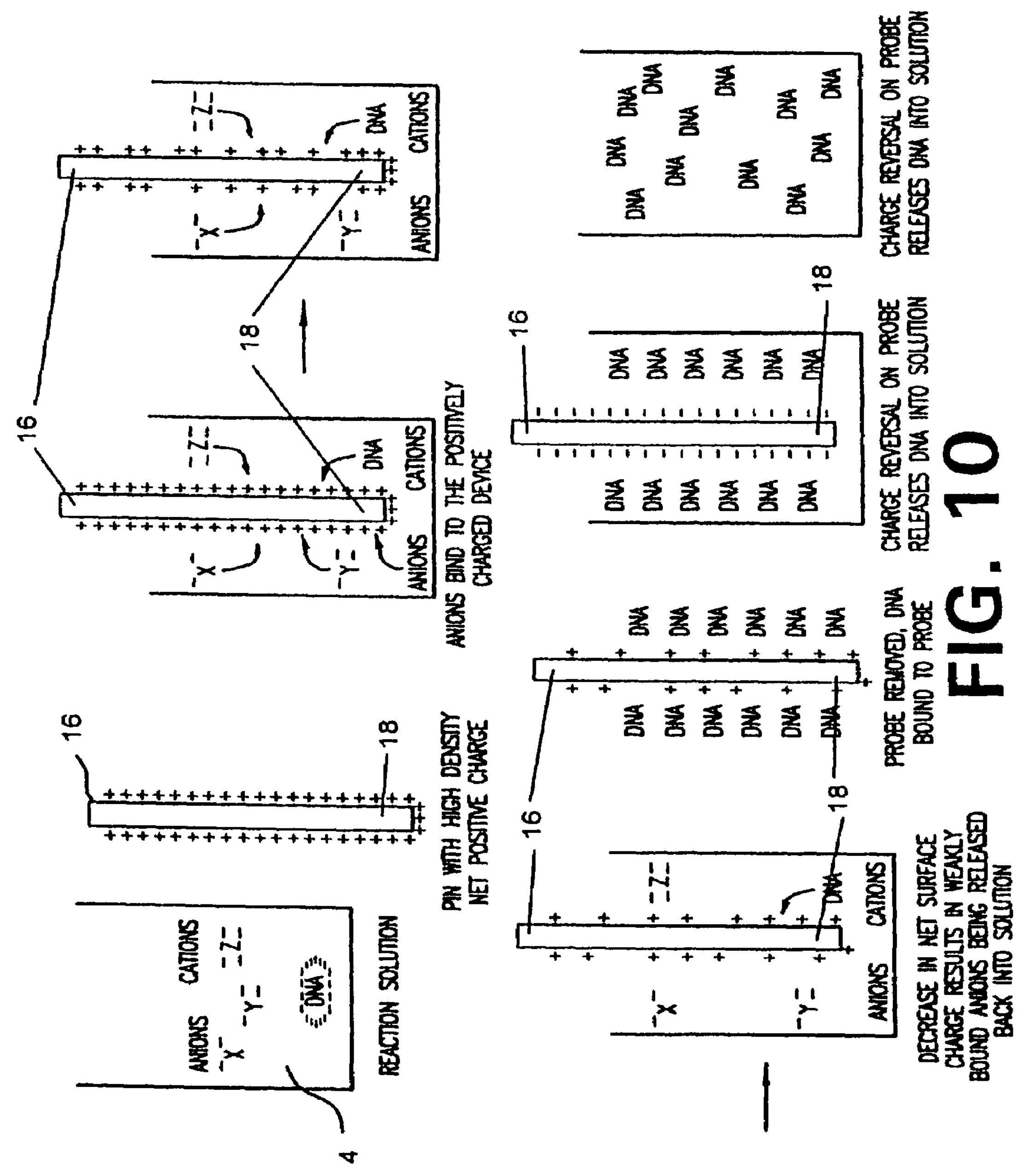
FIG. 10 is a schematic representation of a technique for purification of a liquid using the present invention.
Figure 11:
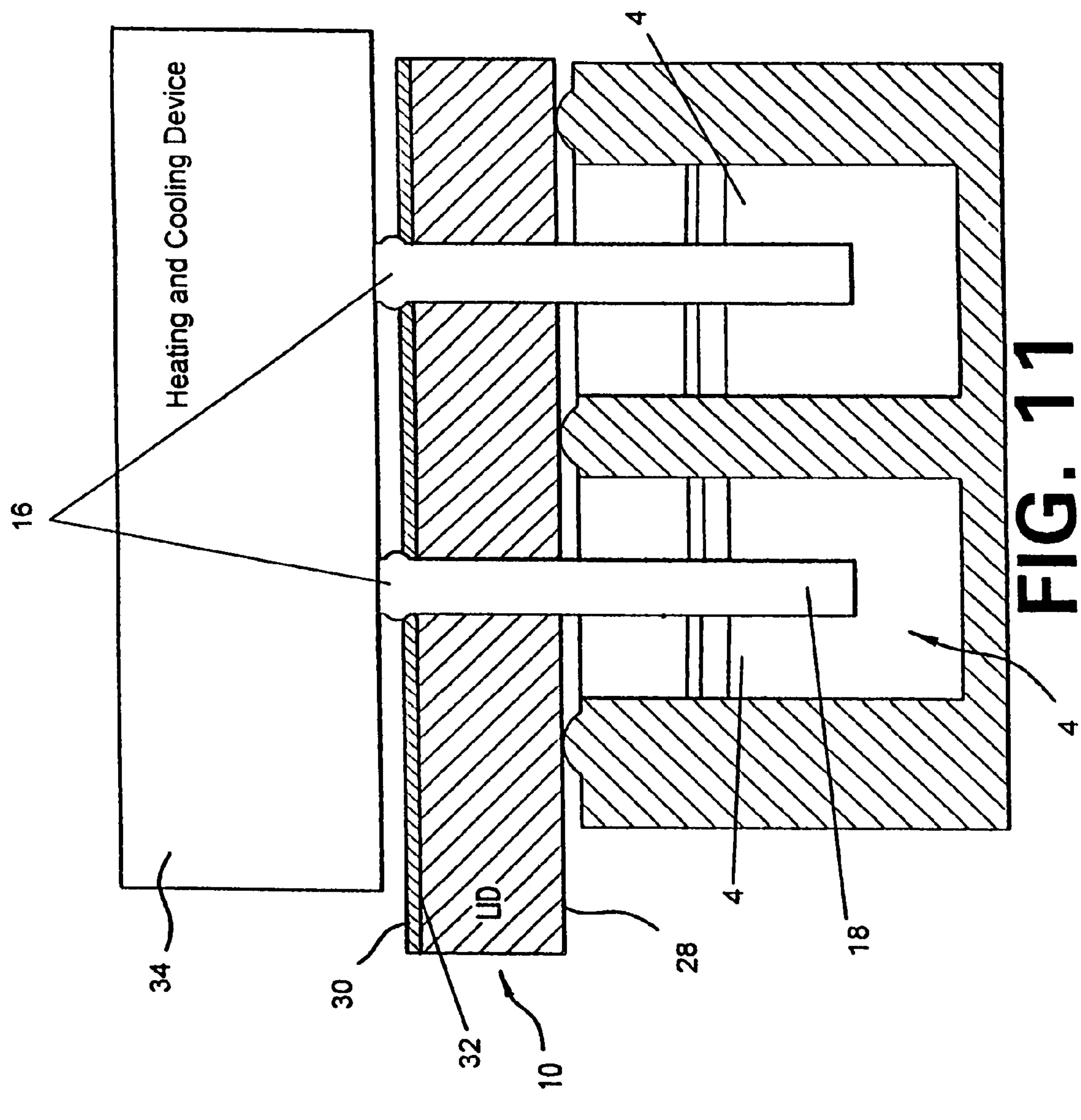
FIG. 11 is a schematic showing application or removal of heat from the pins and from the liquid sample for control of the temperature of the liquid sample.

The upper end 16 of each pin 14 is supported by a resilient layer 30 located on the upper side 32 of the lid 10. The resilient layer 30 is composed of silicone rubber or any suitable resilient material. The pin 14 is able to 'float' on the resilient layer 30; namely, to move in the direction normal to the plane of the upper side 32 of the lid 10 in response to pressure applied to the pin 14 by, say, a peltier device 34 (FIG. 11) or sonic horn 36 (FIG. 9). Because each pin 14 is able to 'float,' minor differences in the height of the pins 14 above the upper side 32 of the lid 10 may be overcome by elastic deformation of the resilient layer 30 so that each pin 14 will contact the peltier device 34 or sonic horn 36.

A plurality of holes 20, substantially the diameter or slightly greater in diameter than the pins 14 are drilled or molded into the lid 10 on a dimensional array corresponding to the dimensions of the well plate 2 that will be used. For example, for a well plate 2 having a 32 by 48 array of wells 6, the holes 20 would be drilled in a 32 by 48 array with a center to center spacing of 2.25 millimeters. The 1536 pins 14 are then inserted through the holes 20 such that the pins 14 protrude beyond the gasket 26. Based on the depth of a standard 1536-well plate 2, the pins 14 will protrude approximately 3 mm from the bottom surface 28 of the lid 10. The pins 14 may protrude from 3 mm for a well plate 2 having 1536 wells 6 to greater than 45 mm for a deep well plate 2 having 96 wells 6.

The plurality of holes 20 and the number and location of pins 14 match the number and location of wells 6 in the well plate 2 for which the lid 10 will be used. For well plates 2 having 96 wells 6, the pattern of holes 20 and pins 14 is a regular array of 8×12 holes 20 and pins 14. For well plates 2 having 384 wells 6, the pattern of holes 20 and pins 14 is an array of 16×24 holes 20 and pins 14. For well plates 2 having 1536 wells 6, the pattern of holes 20 and pins 6 is an array of 32×48 holes 20 and pins 6.

Figure 5:
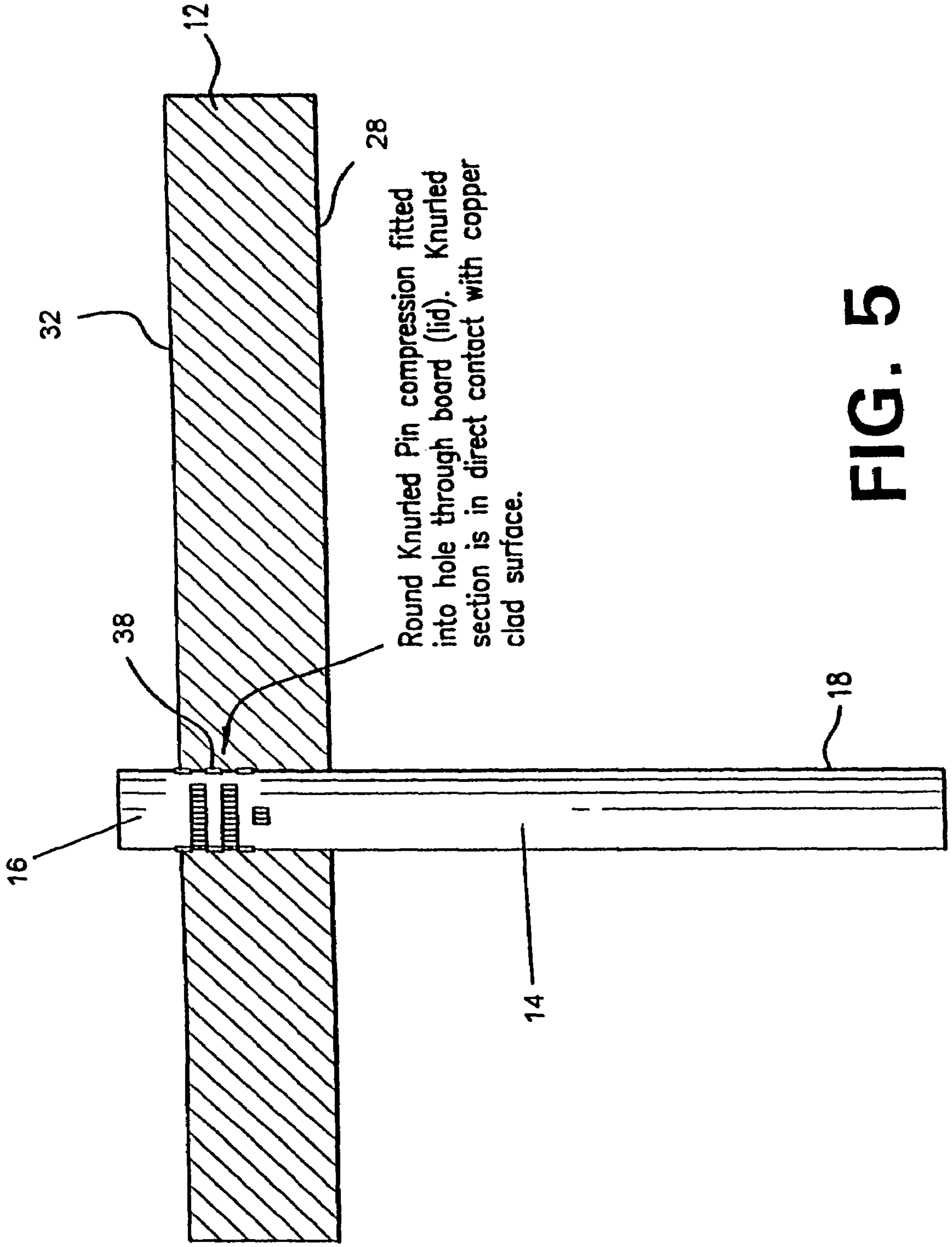
FIG. 5 is an alternative for mounting pins in a lid.
Figure 6:
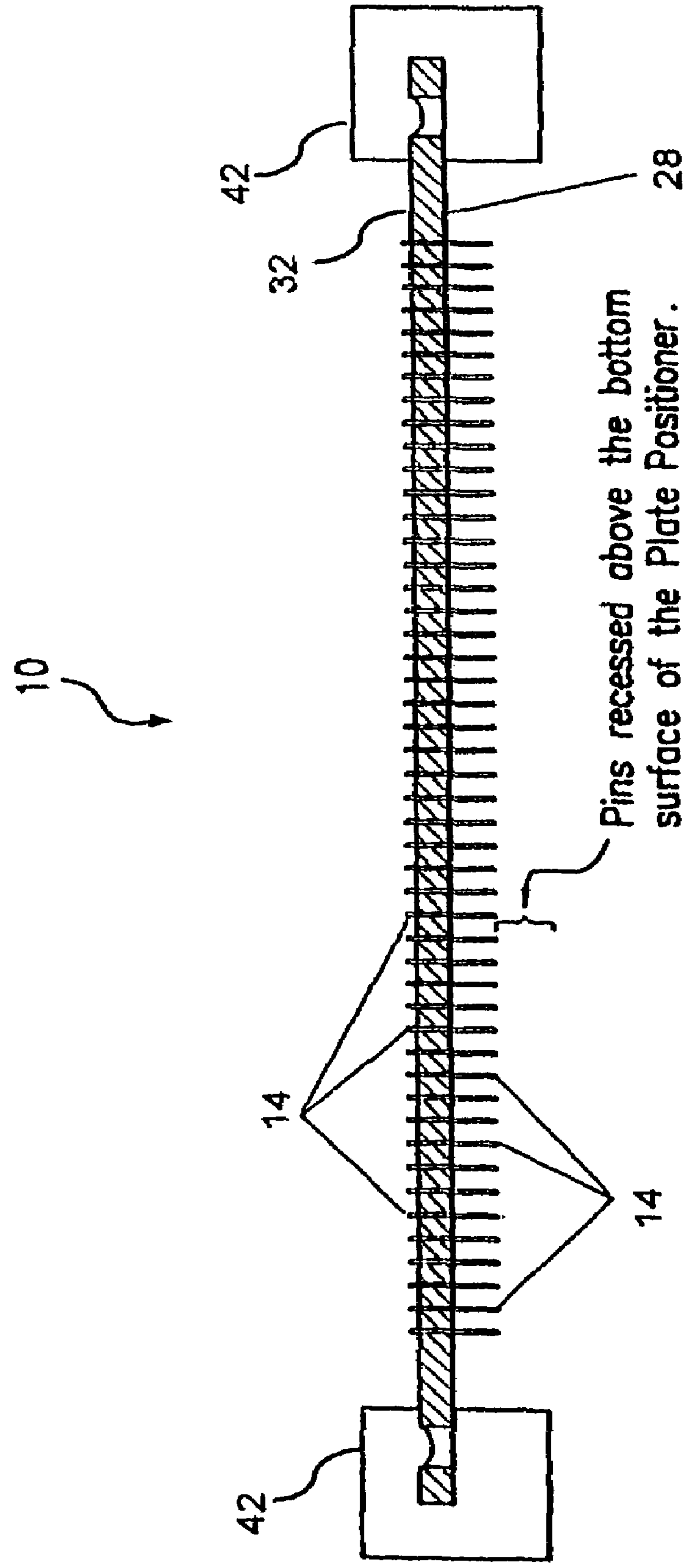
FIG. 6 illustrates a pinned lid including locating ears.
Figure 7:
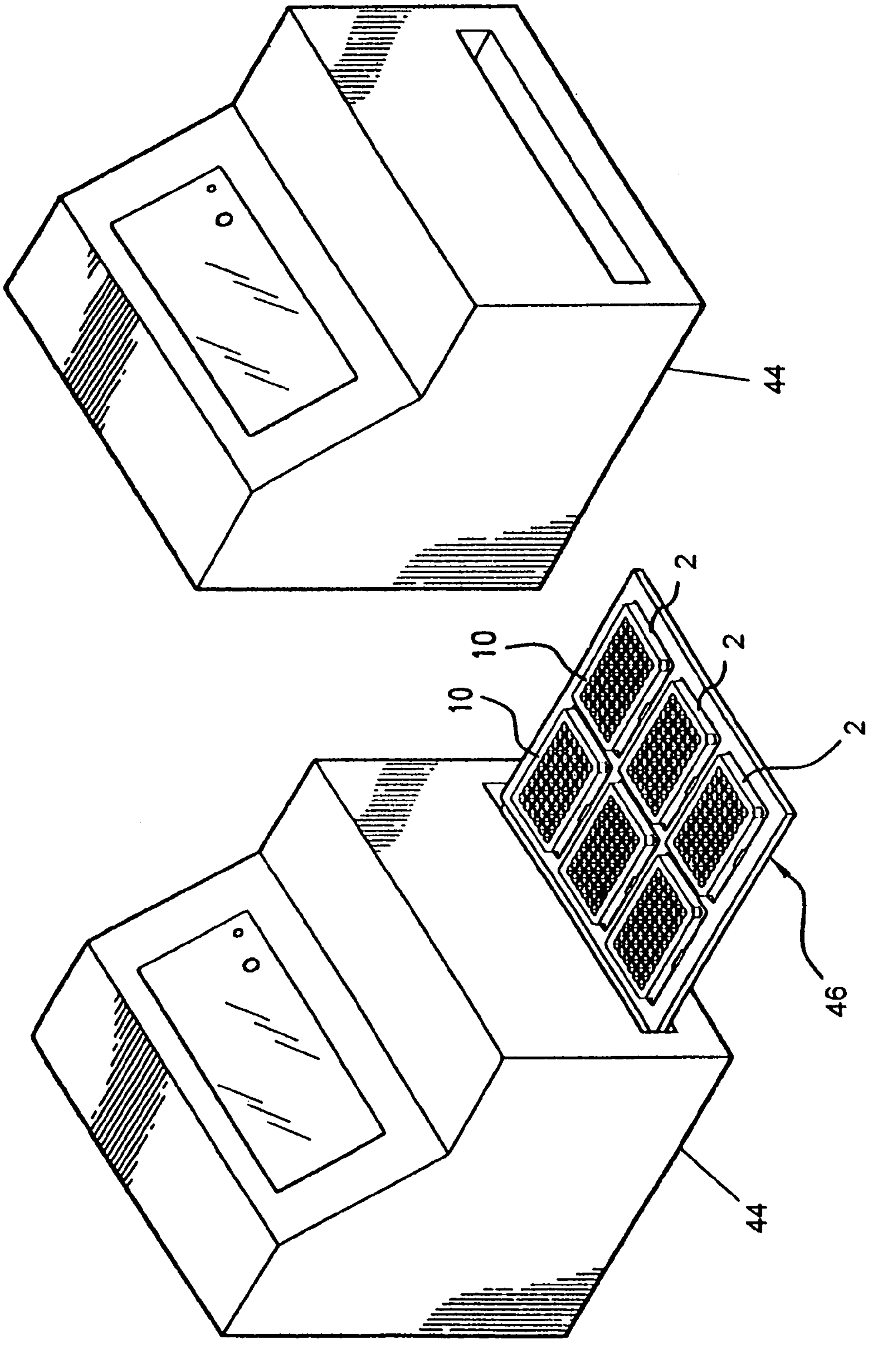
FIG. 7 illustrates an automated apparatus for manipulating samples contained in multiple well plates.
Figure 8:
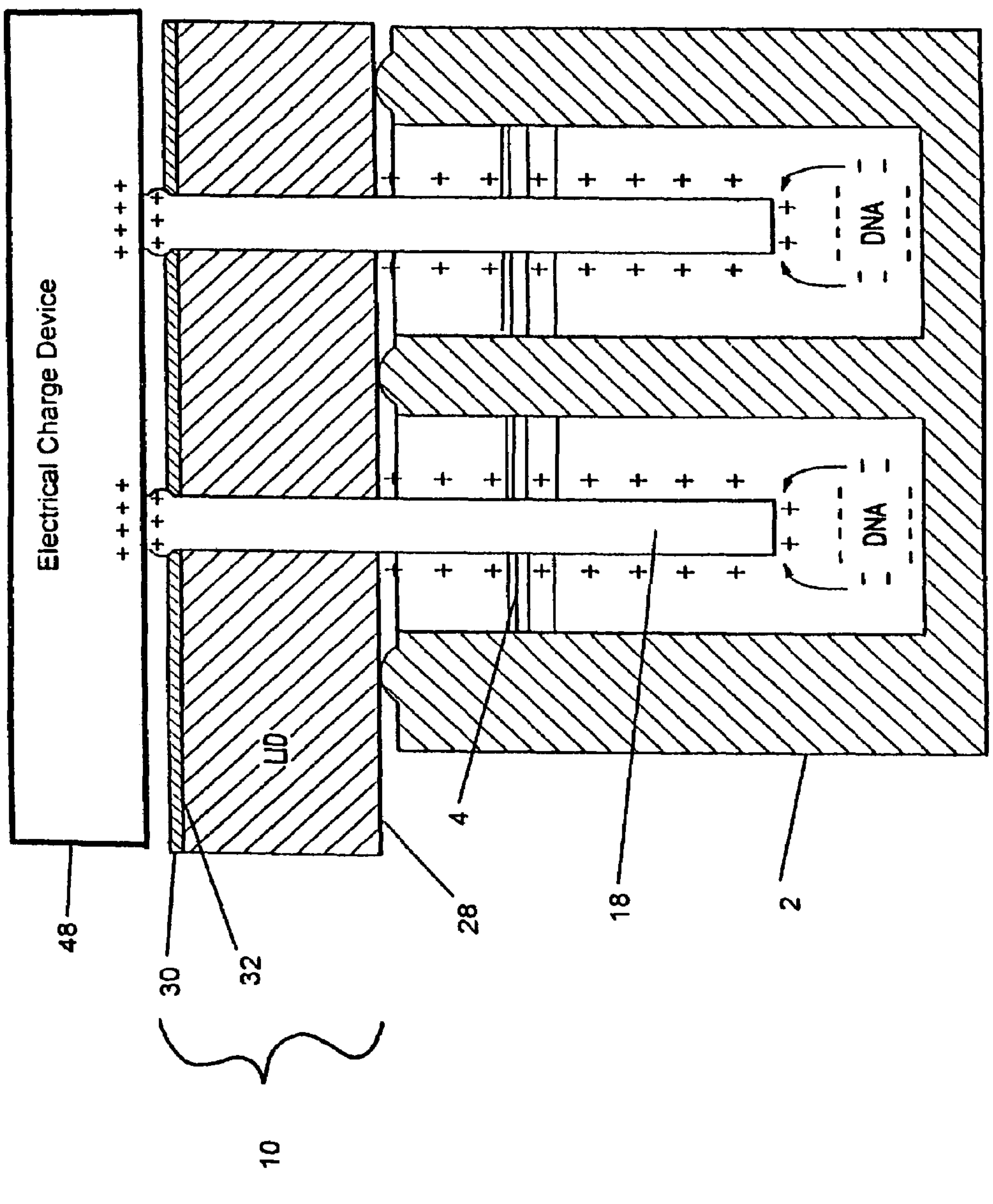
FIG. 8 is a schematic showing application of an electrical charge to the pins by an electrical charge device.

Alternatively, the pins 14 and holes 20 may be sized to be an interference fit and the pins 20 may be retained in the lid by compression. Knurls 38 (FIG. 5) or heads may be formed on or near the top of each pin 14 to assist in the retention of the pins 14 by compression and may prevent the pin 14 from sliding completely through the hole 20 in the lid 10. Other means for attaching the pins 14 may be used, for example, providing the upper surface 32 of lid 10 with a copper cladding and soldering the upper end 16 of each pin 14 to the copper clad surface or bonding the pin 14 to the lid 10 with an adhesive or with heat.

The pins 14 may or may not protrude from the upper side 32 of the lid 10. Depending on the application, the pins 14 should protrude above the upper side 32 of the lid 10 by an amount adequate to allow all pins 14 to engage a peltier device 34, sonic horn 36 or other means for imparting or removing energy to or from the pins 14, but preferably by not more than 1 mm. The pins 14 should be constructed from a material suitable to the application. Where sonication and thermal cycling will be performed on liquid samples 4 in the wells 6 of the well plate 2, the pins 14 should be constructed from a material that will conduct heat and sonic energy and that will not be damaged by the heat and sonic energy. Where electrical charge segregation will be performed, a material capable of carrying an electrical charge on its surface must be incorporated into the pins 14, either in the pin composition or as a coating for all or a portion of the pin.

For example, pins 14 constructed from plain brass may be suitable for sonication. Where sonication, thermal cycling and electrical charge segregation will be performed, pins 14 may be constructed from brass cylindrical stock coated with a 5 micron nickel layer followed by a tin/lead coating. Other materials such as aluminum, gold, copper, or other metals could be used along with certain ceramics and plastics.

A portion of the pin 14 that extends from the bottom side 28 of the lid 10 is designed to make contact with the sample 4 stored in the respective well 6. The pin 14 lengths and the amount of liquid sample 4 may be adjusted to ensure that the pins 14 are at least partially submerged in the liquid sample 4. In the thermal cycling embodiment of the present Invention, the temperature of the upper end 16 of the pins 14 is changed, as by a peltier device 34, thermal block or a jet of heated or cooled air. Accordingly, as the temperature of the upper end 16 of a pin 14 is changed, the temperature of the lower end 18 of the pin 14 is changed, thereby directly heating or cooling the sample 4. In the sonication embodiment, an ultrasonic horn 36 transfers sonic energy directly to the upper end 16 of the pin 14. The sonic energy is transferred through the pin 14 and into the liquid sample 4, sonicating the liquid sample 4. In the electrical charge segregation embodiment, an electrical charge is applied to the upper end 16 of a pin 14, which transmits the charge to the lower end 18 of the pin 14 and hence to the liquid sample 4.

In the sonication and electrical charge segregation embodiments, it is necessary for a pin 14 to be partially submerged in and hence to physically contact the liquid sample 4. In the thermal cycling embodiment, it may not be necessary for a pin 14 to actually contact the liquid sample 4, depending on the application. The close proximity of the heated (or cooled) pin 14 may be adequate to thermally cycle the liquid sample 4 without immersing the pin 14 in the liquid sample 4.

The volume of the pin 14 immersed in the liquid sample 4 may be selected based on the application. For thermal cycling and electrical charge segregation operations, the portion of the pin 14 that is inserted directly into the liquid sample 4 should have a volume of approximately 10% of the liquid sample 4 volume. This comparatively large volume pin 14 insures rapid temperature equilibrium in the sample 4 in during thermal cycling as well as a relatively large surface area for the binding of ions for electrical charge segregation. Also, the pin 14 can be designed to maximize surface area such that heat transfer between the liquid sample 4 and the pin 14 is optimized or the surface area is maximized for electrical charge segregation. The larger the pin 14 cross sectional area, the faster the heat transfer and the greater the surface area for electrical charge segregation (surface area of a cylinder=(pi)$r^2$h). For sonication, different ratios of the immersed volume of the pin 14 to the liquid volume may be appropriate.

If the pin 14 directly contacts the liquid sample 4, the temperature of the sample 4 may be more quickly brought to a desired temperature during thermal cycling by the application of heat or removal of heat from the upper end 16 of the pin 14. Depending on the application, it may not be desirable for the pin 14 to physically contact the liquid sample 4, and a lid 10 may be designed to provide for no physical contact between the pin 14 and the liquid sample 4. Thermal cycling by changing the temperature of the pin 14 may nonetheless change the temperature of the liquid sample 4 because of the proximity of the heated or cooled pin 14 to the liquid sample 4. For sonication or electrical charge segregation, direct contact between the pin 14 and the sample 4 in the well 6 of the well plate 2 is necessary.

The composition and construction of the pins 14 may be determined so as not to interfere, or to interfere only in desired ways, with the reactions and operations to be performed on the liquid samples 4. In some applications, metal pins 14 may be coated with a plastic or other inert material so that the metal will not interfere with the reaction. Pins 14 can be coated with gold, polypropylene, polystyrene, or other metals, plastics, ceramics or other materials that are biologically or chemically inert.

Pins 14 may be cylindrical in shape. Rectangular, hexagonal, elliptical, star or other shaped pins 14 also may also be used. The tip of the pin 14 that protrudes into the liquid sample 4 can be concave or convex, and may have ridges or other structures that can trap small quantities of liquid sample 4. One advantage of the present Invention is that after the liquid samples 4 are manipulated through PCR or cycle sequencing reaction or other operation, the lid 10 can be removed and each pin 14 used as a temporary storage device for a small amount of the liquid sample 4 that was contained in the well 6. If the reaction is to be repeated, the lid 10 with the small quantities of liquid samples 4 attached to the pins 14 may be placed onto a second well plate 2. The small amount of liquid sample 4 on the pins 14 is thereby added to the wells 6 of the second well plate 2 along with an appropriate media to generate new liquid samples 4. The lid 10 can also be used to place small amounts of sample 4 onto other substrates. Each pin 14 may trap a small amount of the liquid sample 4 due to the shape of the pin 14; alternatively, a portion of the sample 4 material may be bound to the pin 14 through electrical charge segregation for transfer to another well plate 2 or for further manipulation.

In thermal cycling operations, the peltier device 34 or other source of heating and cooling selectably may contact some or all of the pins 14. For example, a peltier device 34 may be configured to contact specific rows or columns of pins 14, thereby heating and cooling the specific rows and columns independently from the other pins 14. Similarly, an ultrasonic horn 36 selectably may contact only specified pins 14, sonicating only the liquid samples 4 into which the lower ends 18 of the specified pins 14 are immersed. For selective electrical charge segregation, an electrical charge may be applied to specified pins 14, while a different charge is applied to other of the pins 14. Samples in different wells 6 of a single well plate 2 therefore may be separately manipulated and subjected to different operations.

The Society for Biomolecular Screening (SBS) has proposed a standard well plate 2 configuration for a well plate 2 having 1536 wells 6 which will allow 1536 liquid samples 4 to be simultaneously manipulated. The overall dimensions of the proposed standard well plate 2 having 1536 wells are: 85.48 mm in width, 127.76 mm in length, and 14.35 mm in height. The well-to-well spacing on the 1536-well plate 2 is 2.25 mm center to center. Other well plates 2 in common use include well plates 2 having 96 wells 6 and well plates 2 having 384 wells 6. The well plate 2 having 384 wells 6 is 4.5 mm center to center.

Figure 2A:
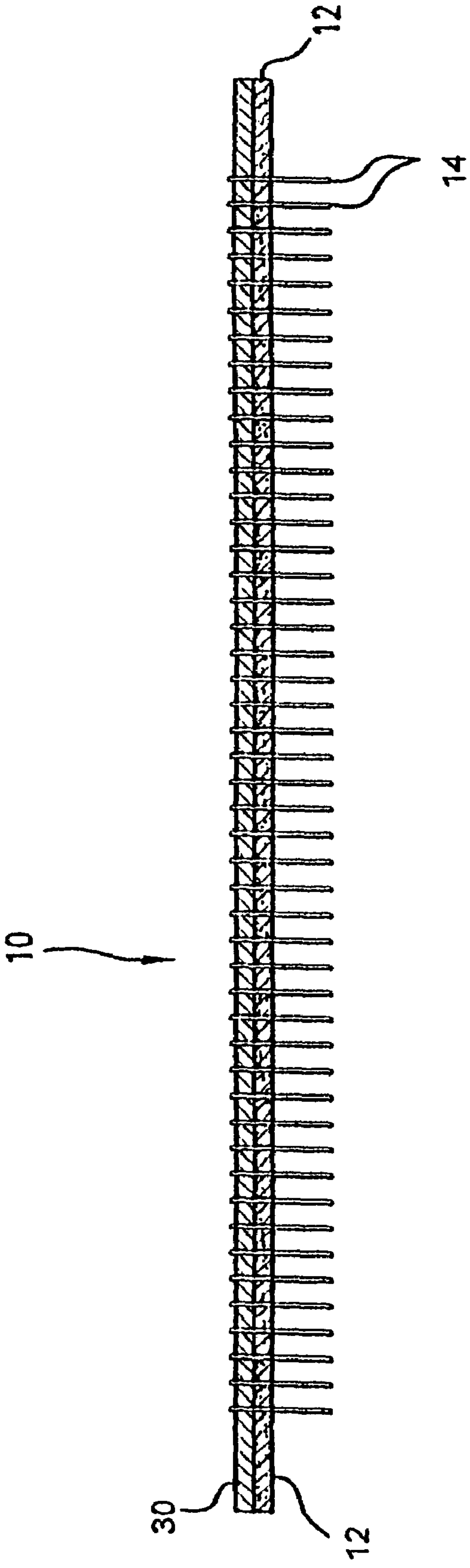
FIG. 2A illustrates a pinned lid.

The well plates 2 of the present Invention conform to the proposed SBS standard in all aspects except for the positioning slots 40 (FIG. 3) to accept and locate the pinned lid 10 (FIG. 2A). Positioning slots 40 are provided on both short sides of the well plate 2 such that the pinned lid 10 can be positioned directly upon the plate 2 without the pins 14 contacting the side walls of the wells 6. The lid 10 includes two or more plastic ears 42. These plastic ears 42 mate with the positioning slots 40 and position the lid 10 on the plate 2 such that the each pin 14 is inserted directly into its corresponding well 6. The ears 40 serve to protect the pins 14 both from contamination and from potential damage.

Multiple well plates 2 containing liquid samples 4 in the wells 6 and having pinned lids 10 may be manipulated by an automated apparatus 44. The automated apparatus 44 may accept from one to six well plates 2, including liquid samples 4 and pinned lids 10. Well plates 2 having any number of wells 6 may be used, including well plates 2 currently available with 96, 384, or 1536 wells 6. When fully loaded with six 1536-well plates 2, the automated apparatus 44 can process more than 9000 samples 4 at one time. The tray 46, onto which the plates 2 are placed, contains an interlock system that positions each plate 2 precisely. This tray 46 can be loaded either manually or robotically with well plates 2 having liquid samples 4 in the wells 6 and having a pinned lid 10. When the tray 46 is moved into the automated apparatus 44, the peltier device 34, sonic horn 36, or electrical charge device 48 (schematically represented in FIG. 12) may be brought into contact with the lid 10. The sequence of operation and parameters of operation of the peltier device 34, sonic horn 36 or electrical charge device 48 are selected by the user to meet the needs of the desired manipulation of the liquid samples 4. The automated apparatus 44 may provide for sonication using the sonic horn 36 to release genetic material followed by thermal cycling using the peltier device 34 for DNA amplification, followed by electrical charge segregation using the electrical charge device 48. Conversely, any sequence of operation may be selected by the user.

When the peltier device 34, sonic horn 36, or electrical charge device 48 is applied to a well plate 2, the peltier device 34, sonic horn 36 or electrical charge device 48 applies a slight pressure to the lid 10. The pressure applied to the lid 10 compresses gasket 26 around each of the wells 6 thus making each well 6 sufficiently air and liquid tight to sufficiently isolating the contents of each well 6 from the contents of every other well 6 and to prevent evaporation, consistent with the requirements of the operation.

Application of pressure by the peltier device 34, sonic horn 36 or electrical charge device 48 also serves to allow the peltier device 34, sonic horn 36 or electrical charge device 48 to operatively contact the upper end 16 of each of the pins 14. Each of the pins 14 is mounted in a hole 20 through the lid 10 and is supported by a resilient layer 30. Application of pressure by the peltier device 34, sonic horn 36 or electrical charge device 48 presses the upper end 16 of the pins 14 into the resilient layer 30, allowing all of the pins 14 to directly contact the peltier device 34, sonic horn 36 or electrical charge device 48 and overcoming any minor differences in height of the pins 14.

The pinned lid 10 may be used for thermal cycling of liquid samples 4 in the wells 6 of a well plate 2. Pins 14 in the pinned lid 10 are constructed of a heat conducting material. The temperatures of the upper ends 16 of the pins 14 are adjusted by using a conventional peltier device 34. Alternatively, other means of heating and cooling the upper end 16 of the pins 14 may be used, such as directing a heated or cooled stream of air over the upper end 16 of the pins 14 or applying a conventional heat/cold block to the upper end 16 of the pins 14. Heat is transmitted the length of the pin 14 and transferred to or from the liquid sample 4, controlling the temperature of the liquid sample 4. The lower end 18 of the pin 14 may be immersed in the liquid sample 4 for thermal cycling, or the lower end 18 of the pin 14 may be in close proximity to the liquid sample 4.

The pinned lid 10 may be used selectably to transfer sonic energy to, or "sonicate," a liquid sample 4. The primary uses of sonication using the pinned lid 10 are to shear large molecules such as nucleic acids or proteins into smaller molecules or to disrupt bacteria, fungal, mammalian or other cells, thereby releasing the contents of the cells into the liquid sample 4. Sonication through use of the pinned lid 10 can also be used to help solubilize particulate matter such as small organic or inorganic molecules or to promote a chemical reaction.

To transfer sonic energy to a liquid sample 4 in the well of a well plate 2, a conventional sonic horn 36 or other such conventional device is brought into physical contact with the upper end 16 of the pin 14, the lower end 18 of which is immersed in a liquid sample 4. The sonic horn 36 is energized, generating sonic energy. The sonic energy from the horn 36 is transferred to the pin 14 in the lid 10, causing the pin 14 to vibrate ultrasonically. The vibrating pin 14 sonicates the liquid sample 4.

Use of a pinned lid 10 to sonicate liquid samples 4 in the wells 6 of a well plate 2 has several advantages over the alternative of a sonic horn 36 with multiple tips for insertion into the wells 6. First, since well plates 2 are commercially available in different heights ranging from approximately 3 mm to greater than 45 mm, it is relatively simple and inexpensive to produce pinned lids 10 of various sizes to mate operably with an intended well plate 2. While construction of a sonic horn 36 with multiple tips for insertion into the wells 6 of a well plate 2 would be possible, such a sonic horn 36 would be expensive. In addition, the use of a pinned lid 10 avoids the expense of constructing multiple sonic horns 36 because only one sonic horn 36 is needed to accommodate the various well plate 2 heights and formats (well plates 2 having 96 wells, 384 wells, or 1536 wells).

A second advantage of using a pinned lid 10 for sonication is that the pinned lid 10 is fully disposable, thus removing the need to clean a horn 36 with multiple tips between uses with the possibility of cross contamination. The pinned lid 10 also prevents airborne contamination of liquid samples 4 during sonication. When a sample 4 is sonicated, microparticles of fluid become airborne. With a sonic horn 36 having multiple tips, it would be difficult to contain the microparticles of fluid within the confines of a single well 6 of the well plate 2. Since the pinned lid 10 contains a gasket 26, each well 6 of the well plate 2 is isolated from all the other wells 6.

In order to demonstrate the utility of the pinned lid 10 for sonication of liquid samples 4 in a well plate 2, the following experiment was conducted. *E. coli* bacterial strain, DH10B was grown overnight to confluence in LB broth. 500 ul of this media was centrifuged in order to concentrate the bacteria and the bacterial pellet was washed 3 times with 200 ul of TAE buffer. After the final wash, the bacteria were resuspended in 200 ul of TAE. 10 ul of this bacterial solution was then placed in each well 6 of a 384 well plate 2 and a pinned lid 10 was applied to the plate 2. A sonic horn 36 with dimensions 85 mm by 120 mm was then brought into contact with the pinned lid 10 and 10 by 1 second pulses was applied to the lid 10. The sonicator was a 1500 watt system used at 50% amplitude. After sonication of the samples 4, the 10 ul samples 4 were removed and centrifuged to pellet insoluble material. Lysis of the bacteria was followed by release of bacterial DNA into solution via horizontal gel electrophoresis. Sonication of the bacterial solution resulted not only in the lysis of the bacteria as observed by the release of DNA into solution but also resulted in the shearing of the bacterial DNA into smaller fragments. Bacterial chromosomal DNA is a circular strand containing approximately 20 kB. After sonication, a small amount of uncleaved DNA is observed at the well/gel interface showing that the uncleaved DNA could not enter the gel. The majority of the DNA was sheared into small 2 kB fragments. The control lane, treated identically except that it was not subjected to sonication shows no release of DNA into solution. Plating of the sonicated and control bacterial samples onto LB agar showed a $10^8$ fold reduction in the number of bacteria present after sonication. These results indicate that the pinned lid 10 can be used successfully to transfer sonic energy from a sonic horn 36 into a sample 4 contained within the wells 6 of a well plate 2. Additionally, these experiments showed that 100% of the wells 6 of a 384 well plate 2 could be sonicated using this technology.

The pinned lid 10 may be used to purify material in a liquid sample 4 in a well 6 of a well plate 2. For example, a positive or negative electrical charge may be placed on the surface of the pins 14 in a pinned lid 10. The electrical charge may be generated or transmitted by a conventional electrical charge device 48, which may be a conventional DC power source or may be a conventional source of electrostatic charge. If a positive charge is applied to the pins 14 then the pins 14 attract negatively charged molecules in the liquid sample 4 in which the pins 14 are placed. The more negatively charged the molecule, the higher the binding affinity of the negatively charged molecule to the positively charged pin 14. The lid 10 and the pins 14 with negatively charged molecules bound to the pins 14 may then be removed from the original liquid sample 4 and placed in a new liquid sample 4 and the electrical charge on the pin 14 can be changed, thereby transfusing the molecules to the new liquid sample 4. In this way, negatively charged molecules can be rapidly removed from the original liquid sample 4 resulting in a purified liquid sample 4. The pin 14 initially may be given a negative charge and thus be used to purify positively charged molecules from the initial liquid sample 4.

A primary use of electrical charged segregation is purification of genetic materials after a nucleic acid amplification event. After completion of the step of thermal cycling of a suitable sample to amplify DNA in the sample, a very high positive charge density may be placed on a pin 14 of the pinned lid 10 by contacting the upper end of the pin with a source of positive electrical charge 48. The surface of the lower end 18 of the pin 14 also acquires a very high positive charge. Anions (including the nucleic acids to be "purified") rapidly bind to the surface of the pin 14. The charge density applied to the pin 14 then is decreased until molecules of only the desired charge (size) remain bound to the pin 14. The pinned lid 10 then is removed from the well plate 2, which removes the pin 14 from the liquid sample 4. The pinned lid 10 is placed on a second well plate 2, which immerses the bottom end 18 of the pin 14 into a second solution. The electrical charge on the pin 14 then is reversed such that the pin 14 becomes an anode containing a net negative charge. The negative charge on the pin 14 repels the negatively charged nucleic acid, and the nucleic acid is released and driven into the second solution and isolated from the reaction products.

As an alternative, when the pin 14 is placed into the second solution, the net positive surface charge may be decreased and not eliminated entirely. This decrease in the charge density of the pin 14 causes smaller nucleic acid fragments to be eluted from the pin 14. By gradually changing the surface charge, a serial purification of nucleic acid fragments based on their relative charge density (size) may be achieved.

The very high net negative charge of DNA amplified by the PCR reaction allows the DNA to be segregated and separated from the unused reactants, other products, and oligonucleotides in a single step. This technique also is used for the purification of proteins, DNA, RNA, or other molecules from 96, 384, 1536, or other well plate 2 formats. The net positive charge on the pin 14 can be precisely regulated by the user to control the binding of anions to the surface of the pin 14. Unlike conventional ion exchange resins that have a fixed net surface charge, the net surface charge on the pin 14 can be selected by the user. At a very high surface density of positive charge, many different anions will bind to the pin 14. As the surface density of positive charge is decreased, the more weakly bound anions will be released into solution. By varying the net surface density of positive charge, purification of the nucleic acid can be achieved. Very precise control of the surface charge will allow separation of nucleic acids that vary only slightly in their net charge (size).

Although this invention has been described and illustrated by reference to specific embodiments, it will be apparent to those skilled in the art that various changes and modifications may be made which clearly fall within the scope of this invention. The present invention is intended to be protected broadly within the spirit and scope of the appended claims.

I claim:

1. An apparatus for manipulating a liquid sample stored in at least one well of a well plate, the apparatus comprising:

a. a lid having an upper side and a lower side, said lower side of said lid engaging the well plate;

b. at least one pin having an upper end and a lower end, said upper end of said at least one pin penetrating said upper side of said lid, said lower end of said at least one pin extending through said lid into the at least one well of the well plate, c. energy transfer means for selectively applying thermal energy, sonic energy, and/or electric charge in any sequence to or from said upper end of said at least one pin, said at least one pin transferring said applied energy or charge to or from the liquid sample.

2. The apparatus of claim 1, further comprising:

a. said lower end of said at least one pin being in physical contact with the liquid sample;

b. said energy transfer means comprising means to apply sonic energy to said upper end of said at least one pin, said at least one pin transmitting said sonic energy through said lid to the liquid sample, said sonic energy sonicating the liquid sample.

3. The apparatus of claim 2, said means to apply sonic energy to said upper end of said at least one pin comprising a sonic horn.

4. The apparatus of claim 3 further comprising:

a. said sonic horn applying a mechanical pressure to said at least one pin;

b. said at least one pin being resiliently connected to said lid such that said pin may move in response to said mechanical pressure by said sonic horn.

5. The apparatus of claim 4 said resilient connection of said at least one pin to said lid further comprising:

a. said lid defining a hole conforming generally to said at least one pin;

b. said hole having a cross-sectional area operably the same as or larger than a cross-sectional area of said pin, said pin being disposed within said hole;

c. a resilient layer being disposed on the upper side of said lid;

d. said upper side of said lid defining a plane, said at least one pin engaging said resilient layer such that said mechanical pressure applied to said at least one pin causes said at least one pin to move in a direction normal to said plane, said motion being resiliently opposed by said resilient layer.

6. The apparatus of claim 5, further comprising: said engagement between said lower side of said lid and the well plate being a sealable engagement, said degree of sealable engagement being selected so as to prevent escape of the liquid sample from the well when said means to apply sonic energy is sonicating the liquid sample.

7. The apparatus of claim 6 further comprising: a resilient gasket disposed between said lower side of said lid and the well plate, said sealable engagement between said lower side of said lid and the well plate comprising said gasket sealably engaging said well plate and said gasket sealably engaging said lid.

8. The apparatus of claim 7 further comprising: said energy transfer means comprising means to regulate the temperature of the upper end of said at least one pin, thereby regulating the temperature of the lower end of said at least one pin and regulating the temperature of the liquid sample.

9. The apparatus of claim 8, said means to regulate the temperature of the upper end of said at least one pin comprising a peltier device, a heat block, or a stream of heated or cooled air.

10. The apparatus of claim 9, further comprising:

a. said at least one pin being capable of supporting an electrical charge;

b. said energy transfer means comprising means to selectively apply an electrical charge to said at least one pin.

11. The apparatus of claim 10, further comprising:

a. said means to selectively apply an electrical charge to said at least one pin comprising applying an electrical charge to said upper end of said at least one pin;

b. said electrical charge being of sufficient magnitude and duration so as to cause electrical charge segregation of the liquid sample.

12. The apparatus of claim 1 further comprising: said at least one pin being resiliently connected to said lid such that said pin may move in response to a mechanical pressure applied to said upper end of said pin.

13. The apparatus of claim 12 said resilient connection of said at least one pin to said lid further comprising:

a. said lid defining a hole conforming generally to said at least one pin;

b. said hole having a cross-sectional area operably the same as or larger than a cross-sectional area of said pin, said pin being disposed within said hole;

c. a resilient layer being disposed on the upper side of said lid;

d. said upper side of said lid defining a plane, said at least one pin engaging said resilient layer such that said mechanical pressure applied to said at least one pin causes said at least one pin to move in a direction normal to said plane, said motion being resiliently opposed by said resilient layer.

14. A method for manipulating a liquid sample in a well of a well plate comprising the steps of:

a. placing the liquid sample in the well of the well plate;

b. placing a lid on the well plate, said lid having an upper side and a lower side, said lid having at least one pin having an upper end and a lower end, said pin penetrating said lid, said upper end of said pin extending to said upper side of said lid, said lower end of said pin extending into the well of the well plate, said lower end of said pin physically contacting the liquid sample;

c. selectively and in any sequence applying thermal, sonic, and/or electrical energy to said upper end of said at least one pin, said pin transmitting said energy to said lower end of said at least one pin.

15. The method of claim 14, further comprising: said sonic energy being transmitted by said at least one pin to the liquid sample, said sonic energy sonicating the liquid sample; said lower side of said lid sealably engaging the well plate with a degree of sealable engagement selected so as to prevent an escape of the liquid sample during sonication of the liquid sample.

16. The method of claim 15 further comprising: said thermal energy being applied or removed by adding heat or removing heat from said upper end of said at least one pin, thereby adding or removing heat from the liquid sample.

17. The method of claim 15 further comprising: said applying of said electrical energy comprising applying an electrical charge of a sufficient magnitude and duration to said upper end of said at least one pin to attract an ion having an opposite charge from the liquid sample and reversibly binding said ion to said lower end of said pin.

18. The method of claim 17 further comprising:

a. removing said lid from the well plate while said ion is bound to said at least one pin;

b. engaging said lid with a second well plate, said second well plate having a well containing an appropriate reagent, said reagent physically contacting said lower end of said at least one pin;

c. adjusting said electrical charge applied to said pin to selectably release said ion from said pin into said reagent.

* * * * *